United States Patent [19]

Mlotfijalkowski

[11] 3,944,828

[45] Mar. 16, 1976

[54] HYDROPHOBIC POWDERED DEVELOPER FOR FLUORESCENT PENETRANT INSPECTION

[75] Inventor: Adolf Mlotfijalkowski, Lincolnwood, Ill.

[73] Assignee: Magnaflux Corporation, Chicago, Ill.

[22] Filed: Sept. 30, 1974

[21] Appl. No.: 510,396

[52] U.S. Cl. .............................................. 250/302
[51] Int. Cl.² ........................................ G01N 21/16
[58] Field of Search ........ 250/302; 73/104; 252/408

[56] References Cited
UNITED STATES PATENTS 3,558,882  1/1971  Mlot-Fijalkowski ............... 250/302

*Primary Examiner*—Davis L. Willis
*Attorney, Agent, or Firm*—Hill, Gross, Simpson, Van Santen, Steadman, Chiara & Simpson

[57] ABSTRACT

A method for detecting surface discontinuities in a part which comprises applying a non-water miscible fluorescent penetrant to the part to permit the penetrant to enter and become lodged in surface discontinuities, applying an emulsifying agent to the part to emulsify excess penetrant, washing the part with water to remove the emulsifying agent and emulsified penetrant while leaving penetrant lodged in the discontinuities, and thereafter applying particles of a dry hydrophobic developer over the part so that upon removal of excess developer, the part may be inspected for penetrant exuded out of the discontinuities and into the hydrophobic particles.

7 Claims, No Drawings

HYDROPHOBIC POWDERED DEVELOPER FOR FLUORESCENT PENETRANT INSPECTION

BACKGROUND OF THE INVENTION

1. Field of the Invention

This invention is in the field of nondestructive testing of objects by means of the penetrant inspection technique, and utilizes hydrophobic developing particles to render indications contrastingly visible to the background.

2. Description of the Prior Art

The present invention is concerned with the well-known "post-emulsification" technique of removing excess penetrant from a test piece being tested by the penetrant inspection method. The post emulsification technique is described completely in the DeForest et al. U.S. Pat. No. 2,806,959. As noted in that patent, the method involves employing an oily liquid penetrant having excellent penetrating properties but being immiscible with water and being substantially free of any emulsifying agent. The oily penetrant is then treated with an emulsifying agent which, by substantially static contact with the penetrant, renders the latter superficially water-emulsifiable. In a subsequent washing step with water, it is only the superficial emulsified layer of the penetrant that is removed with the excess of emulsifying agent. Any emulsified penetrant that has penetrated the surface discontinuities remains in such discontinuities and serves to indicate the existence and location thereof by the contrasting color effect that is obtained upon application of a developer to the surface. Where the penetrant is colored with a fluorescent dye dissolved in the penetrant, the inspection is carried out under "black" or ultraviolet light.

This type of process has been widely used commercially and is quite successful because it is capable of determining the presence of relatively shallow and relatively wide cracks, as well as the presence of defects having very fine surface openings. This is so because the non-water miscible penetrant is not washed out of such wide, shallow cracks and is better able to enter into the finer surface defects.

A specific improvement on the DeForest et al. patent is found in the Parker U.S. Pat. No. 2,978,418 which describes an improved emulsifier for the post emulsification process, the emulsifier containing from 1 to 20 percent by volume of tri-butoxyethyl phosphate.

Another type of improved emulsifier for the post emulsification process is described in Borucki U.S. Pat. No. 3,401,556. That patent deals with an emulsifier composition which is free from sulfur, chlorine and phosphorus and includes effective proportions of 1. a water miscible alkanol amine,
2. tallol,
3. a water miscible polymerized monohydroxy oxy 1,2-propylene aliphatic monoether which functions as a coupling agent,
4. a non-ionic lauroyl diethanol amine wetting agent,
5. an alkyl aryl polyether alcohol which imparts enhanced water washability to the resulting emulsifier,
6. an isoparafinic hydrocarbon as a solvent, and
7. water.

Still another emulsifier suitable for use in a post emulsification process is disclosed in Magdalin U.S. Pat. No. 3,585,853. This emulsifier is an aerosol foam-forming composition which includes water, a surfactant, a foaming agent, a coupling agent, and optionally a corrosion inhibitor.

The dry developers currently being used in the post emulsification-type process may consist of mixtures of silica aerogels, hydrated alumina aerogels and talc. These materials, however, are all hydrophilic which requires that the part, after emulsification with the emulsifier, be thoroughly washed with water and dried completely before the dry developer is applied. Otherwise, the finely divided hydrophilic particles pick up water and form a thin cake on the surface of the part which tends to obscure indications caused by penetrant exuding out of the cracks and into the powder.

SUMMARY OF THE INVENTION

The present invention makes use of a dry, fluffy developer of an average particle size of less than 1 micron and consisting of hydrophobic particles such as specially treated silica aerogels or calcium carbonate. Through the use of the improved developer of the present invention, it is no longer necessary to dry the surface of the part thoroughly after the emulsifier has been water washed to effect its removal. For ease in inspection, it is desirable that standing droplets of water be removed and this can be done conveniently by an air stream. The hydrophobic developer particles can be applied to the part while it is still moist. The application of the powder always finds the penetrant residues even if water droplets are present in other areas of the part because the penetrant residues are themselves hydrophobic so that any residual water will not film over such deposits. Finally, the excess developer powder can be removed by means of an air blast or the like and the part is thereafter inspected in black light to cause fluorescence of the dye in the penetrant.

DESCRIPTION OF THE PREFERRED EMBODIMENTS

In accordance with the present invention, I carry out the conventional post emulsification process using a water immiscible fluorescent penetrant and an emulsifying agent to remove excess penetrant in the usual way. The residual emulsifying agent and the emulsified penetrant are then washed in water, again in the usual manner, but the water which remains is not dried thoroughly as it has been in the past. It is desirable for the purposes of the present invention to direct an air blast at the water washed part so as to remove standing droplets of water, while leaving the surface still reasonably moist. Further drying to absolute dryness can, of course, be carried out, but it is not necessary and economically unattractive. The removal of excess water by an air blast improves the condition of the part for handling by the ultimate inspectors but is not essential. Furthermore, excess hydrophobic developer particles are easy to remove by an air blast even if they settle in wet areas of the parts.

The process of the present invention can make use of conventional water immiscible penetrants and emulsifying agents presently available on the market. The following formulations illustrate several oil base penetrants which can be so used.

EXAMPLE I

Vehicle

| | | |
|---|---|---|
| | Refined kerosene | 40% by volume |
| | No. 60 Lube oil | 45% by volume |
| | Dye solvent | 15% by volume |
| Dye | | |
| | Fluorol 7GA | 0.35 g./100 ml. |

In the above formulation, the dye solvent can be an alkyl-aryl phosphate or other dye solvents which are miscible with the petroleum oils used. In general, aralkyl esters have been found to be excellent solvents for the dye.

"Fluorol 7GA" is a fluorescent dye supplied by General Dyestuffs Corporation. Other soluble fluorescent dyes, of course, may be used.

Still other examples of fluorescent dye penetrants are given in the following examples.

EXAMPLE II

Vehicle

| | | |
|---|---|---|
| | Naphtha | 75% by volume |
| | Partially hydrogenated terphenyl | 25% by volume |
| Dye | | |
| | 2,5 dimethyl coeroxen | 0.8 mg./100 ml. |

EXAMPLE III

Vehicle

| | | |
|---|---|---|
| | Kerosene (high flash) | 40% by volume |
| | No. 60 Lube oil | 30% by volume |
| | Partially hydrogenated terphenyl | 20% by volume |
| | Alkyl aryl phosphate | 10% by volume |
| Dye | | |
| | Fluorol 7GA | 0.35 mg./100 ml. |

Examples of suitable emulsifier compositions are given in the following examples:

EXAMPLE IV

| | |
|---|---|
| No. 2 fuel oil | 57% by volume |
| Tall oil (medium viscosity) | 30% by volume |
| Saturated aqueous solution of borax | 1% by volume |
| Triethanol amine | 12% by volume |

EXAMPLE V

| | |
|---|---|
| Kerosene | 23% by volume |
| Refined tall oil | 55% by volume |
| Triethanol amine | 22% by volume |

The emulsifying composition need not be a mixture but it may consist of single ingredients such as Twitchel oil No. 7231 which is a mixture of straight petroleum oils with sulfonated oils and has a relatively high viscosity. Still other emulsifying agents can be used alone and include various non-ionic surface active agents such as polyoxyethylene sorbitol oleate laurate, alkyl aryl polyether alcohols such as "Triton X100," and various alkyl aryl sulfonates.

The preferred dry developer according to the present invention is an ultrafine silica aerogel which has been treated to make it hydrophobic. Typically, such materials are produced commercially from a silicon dioxide aerosol obtained by flame hydrolysis. For each 100 square meters of surface area, such material has about 0.5 millimol silanol groups making it hydrophilic. About 75 percent of these silanol groups can be chemically reacted with dimethyl dichlorosilane to produce a product having about 0.7 millimol of chemically combined methyl groups per 100 square meters of surface area. The silica thus becomes hydrophobic. The hydrophobic silica differs from the hydrophilic starting material particularly in its carbon content which ranges from about 0.9 to 1.3 percent per 100 square meters. The specific surface area is on an average of about 15 percent lower than the surface area of the starting hydrophilic material. The hydrophobic nature of the material can be appreciated from the fact that the hydrophobic silica aerogel adsorbs only 0.8 millimol of water even at 80 percent relative humidity, whereas the hydrophilic material adsorbs 20 times this amount.

Another suitable material for use in the present invention is a hydrophobic calcium carbonate which is not an aerogel but is a submicron particle size and does have definite hydrophobic properties. The particles may be coated with approximately 3.5 percent by weight coconut oil to render them hydrophobic.

The use of the hydrophobic dry developer has the distinct advantage of eliminating the necessity of thorough drying from the standard processing sequence of a post emulsification penetrant system. All that is needed, in place of thorough drying, amounts of the removal of droplets of water by means of an air blast.

It was found that the application of hydrophobic silica aerogel particles, when processed by a standard post emulsification method and air sprayed instead of drying, produced excellent indications equal in quality and brightness to those obtained by using standard dry power developers.

The process of the present invention is also applicable to water washable penetrants to give indications, but not with the reliability which is achieved with water immiscible penetrant composition.

It should be evident that various modifications can be made to the described embodiments without departing from the scope of the present invention.

I claim as my invention:

1. The method of detecting surface discontinuities in a part which comprises applying a fluorescent penetrant to said part to permit said penetrant to enter and become lodged in surface discontinuities, applying an emulsifying agent to said part to emulsify excess penetrant, washing the part with water to remove emulsifying agent and emulsified penetrant while leaving penetrant lodged in said discontinuities, and while the surface of said part is still moist, applying particles of a dry hydrophobic developer over said part, removing excess developer, and thereafter inspecting said part for penetrant exuded out of said discontinuities and into said particles.

2. The method of claim 1 in which water droplets remaining after washing are removed by means of an air stream.

3. The method of claim 1 in which said hydrophobic developer comprises a silica aerogel.

4. The method of claim 1 in which said hydrophobic developer comprises calcium carbonate.

5. The method of claim 1 in which excess hydrophobic developer particles are removed by means of an air spray.

6. The method of claim 1 in which the average particle size of said hydrophobic developer particles is not more than 1 micron.

7. In the method of non-destructive testing in which a penetrant is applied to the surface of a piece, excess penetrant is removed while leaving penetrant trapped in any surface discontinuities, and a developer is applied over the surface after excess penetrant removal, the improvement which comprises employing a dry, hydrophobic powder as the developing agent.

* * * * *